{ United States Patent [19] } { [11] Patent Number: 4,791,926 }

Fry { [45] Date of Patent: Dec. 20, 1988 }

[54] METHOD OF CONTROLLING LASER ENERGY REMOVAL OF PLAQUE TO PREVENT VESSEL WALL DAMAGE

[75] Inventor: Stephen M. Fry, Del Mar, Calif.

[73] Assignee: Baxter Travenol Laboratories, Inc., Deerfield, Ill.

[21] Appl. No.: 119,167

[22] Filed: Nov. 10, 1987

[51] Int. Cl.$^4$ .............................................. A61B 17/36
[52] U.S. Cl. ............................ 128/303.1; 219/121.62
[58] Field of Search ..................... 128/303.1, 395–398; 219/121 LA, 121 LB

[56] References Cited

U.S. PATENT DOCUMENTS

| | | | |
|---|---|---|---|
| 4,266,547 | 5/1981 | Komiya | 128/395 |
| 4,316,467 | 2/1982 | Muckerheide | 219/121 LB |
| 4,469,098 | 9/1984 | Davi | 128/303.1 |
| 4,476,512 | 10/1984 | Sunago et al. | 361/103 |
| 4,587,972 | 5/1986 | Morantte | 128/303.1 |
| 4,653,495 | 3/1987 | Nanuni | 128/303.1 |
| 4,718,417 | 1/1988 | Kittrell et al. | 128/398 |

FOREIGN PATENT DOCUMENTS

| | | |
|---|---|---|
| 0069930 | 1/1983 | European Pat. Off. ......... 128/303.1 |
| 8201669 | 6/1983 | PCT Int'l Appl. . |
| 2125986 | 8/1983 | United Kingdom . |

OTHER PUBLICATIONS

Macruz, Ribeiro, Brum, Pasqualucci, Mnitentag, Bozinis, Marques, Jatene, Luiz, Decourt, and Armelin; "Laser Surgery in Enclosed Spaces a Review" Lasers in Surgery and Medicine 5:199–218 (1985), pp. 200–217.

Eugene, McColgen, Hammer-Wilson, Moore-Jeffries, and Berns, "Laser Applications to Arterlosclerosis: Angioplasty, Angioscopy, and Open Endarterectomy" Lasers in Surgery and Medicine 5:309–320 (1985), pp. 310–319.

Cothren, Hayes, Kramer, Sacks, Kittrell, and Field, "A Multifiber Catheter with an Optical Shield for Laser Angiosurgery" Lasers in the Life Sciences, Jul. 1986, pp. 1–12.

Cothren, Hayes, Kramer, Sacks, Kittrell, Feld, A Multiplier Catheter with an Optical shield for Laser Angiosurgery, Abstract, Cariology Laser Therapy, CCF/M17, pp. 34–44+FIGS. 1–6.

Isner, Donaldson, Funai, Deckelbaum, Pandian, Clarke, Konstam, Salem, and Bernstein, Factors Contributing to Perforations Resulting from Laser Coronary Angioplasty: Observations in an Intact Human Postmortem Preparation of Intraoperative Laser Coronary Angioplasty, Cardio-Laser Isner, pp. II-191-II-199, vol. 72.

Kaplan, Case, Choy, Vascular Recanalization with the Argon Laser: The Role of Blood in the Transmission of Laser Energy, 1985 Alan R. Liss, Inc., Lasers in Surgery and Medecine 5:275–279 (1985).

Lee, Cham, Ideda, Rink, Dukich, Peterson, Lee, Reis, and Mason, Applicability of Laser to Assist Coronary Balloon Angioplasty, American Heart Journal, vol. 110, No, 6, Dec. 1985, pp. 1233–1236.

Abela, Normann, Cohen, Franzini, Feldman, Crea, Fenech, Pepine, and Conti, Laser Recanalization of Occluded Atherosclerotic Arteries in Vivo and in Vitro (List continued on next page.)

Primary Examiner—Max Hindenburg
Attorney, Agent, or Firm—Loyal M. Hanson

[57] ABSTRACT

A method of controlling laser energy removal of plaque or other obstructions from a vessel of the cardiovascular system includes advancing a laser delivery catheter to a position in proximity with a targeted lesion, placing a laser energy sensor device in a monitoring position adapted to sense laser energy from the catheter that passes beyond the lesion, and controlling the laser energy according to the output of the sensor. An intraoperative approach places the sensor external to the vessel, while a percutaneous approach places the sensor within the vessel utilizing an additional sensor fiber on the catheter that extends beyond the lesion to the monitoring position. Each fiber in a multifiber laser delivery bundle may be controlled according to sensor output for precision aiming and improved laser control.

16 Claims, 1 Drawing Sheet

OTHER PUBLICATIONS

Cardio Laser, vol. 71, No. 2, Feb. 1985, pp. 403–411.
Wexler, Selzer, Murphy-Chutorian, Ginsburg, Lasers: Technology and Potential Use in Atherosclerosis, Abstract for Society of Cardiovascular and Interventional Radiology, 10th Annual Course, Stanford University Medical Center, Stanford, California 94305, pp. 125–132.

Cothren, Kittrell, Hayes, Willett, Sacks, Malk, Ehmsen, Bott-Silverman, Kramer, and Feld, Controlled Light Delivery for Laser Angiosurgery, Quantum Electronics Letters, vol. QE-22, No. 1, Jan. 1986, pp. 4–7.
Special Issue: Laser Application to Occlusive Vascular Disease; Guest Editors: Berns and Mirhoseini, Lasers in Surgery and Medicine, Vo.. 5, No. 3, 1985, pp. 269–270: Laser Endarterectomy; pp. 199–217: Laser Surgery in Enclosed Spaces: A Review.

METHOD OF CONTROLLING LASER ENERGY REMOVAL OF PLAQUE TO PREVENT VESSEL WALL DAMAGE

BACKGROUND OF THE INVENTION

1. Technical Field

This invention relates generally to laser energy removal of thrombi or other obstructions in vessels of the human body, and more particularly to a new and improved method of controlling laser energy during removal to prevent vessel wall damage.

2. Background Information

The possibility of vessel wall damage complicates laser removal of obstructions. Just as laser irradiation can vaporize a targeted lesion, it can damage the untargeted vessel wall. Thus, the physician needs a method of precisely controlling laser delivery.

Advancement of a laser catheter within the vessel up to the lesion may be monitored by cineangiography techniques, and the ablation process monitored by computer analysis of luminescence returning from the lesion, but firing, spotting the effect, and then deciding the next action may nevertheless be somewhat hit-and-miss. The laser beam may miss the target by passing through an existing channel in the lesion or it may break through the lesion, in either case threatening the vessel wall.

In other words, a miss or breakthrough can pass sufficient laser energy beyond the lesion to the vessel wall before detection and cause significant vessel wall damage before aim adjustment or laser deactivation. Consequently, it is desirable to have a new and improved method of laser delivery that overcomes this concern—one adapted to sense a miss or breakthrough as it occurs so that the laser can be deactivated before it damages the vessel wall and the aim readjusted if desired.

SUMMARY OF THE INVENTION

This invention recognizes the problems associated with the prior art and provides a new and improved method of removing obstructions with the desired attributes.

Briefly, the above and further objects of the present invention are realized by monitoring the laser energy distally to the lesion and controlling the laser accordingly. When a miss or breakthrough occurs that allows more than a predetermined level of laser energy to pass beyond the lesion, the laser is immediately deactivated before damage to the vessel wall occurs. Combining these steps with delivery through a bundle of individually controlled fibers, enables precision aiming and superior laser control for more effective and safer removal.

Generally, the method includes advancing a laser delivery catheter to a position in proximity with a targeted lesion, placing a laser energy sensor device in a monitoring position adapted to sense laser energy from the catheter, guidewire, or fiber that passes beyond the lesion, propagating laser enegy through the catheter toward the lesion, and controlling the laser energy according to the output of the sensor. The sensor output is processed by suitable circuitry to either alert the physician or automatically deactivate the laser energy, or both.

Recognizing that laser energy can be seen through the vessel wall, an intraoperative approach utilizes a sensor device placed in the monitoring position external to the vessel. Here it senses laser energy passing through the vessel as an indication of passing beyond the lesion to provide an output that is processed for control purposes.

In a percutaneous approach, the sensor is placed within the vessel. This is accomplished in one form of the invention with an additional sensor fiber on the catheter that extends beyond the one or more laser delivery fibers. The distal end of the sensor fiber is placed through the lesion to the monitoring position, and the output is processed as described above to provide at least one of a human sensible and an electrical control signal.

The above mentioned and other objects and features of this invention and the manner of attaining them will become apparent, and the invention itself will be best understood, by reference to the following description taken in conjunction with the accompanying illustrative drawings.

DESCRIPTION OF THE PREFERRED EMBODIMENTS

Figure 1:
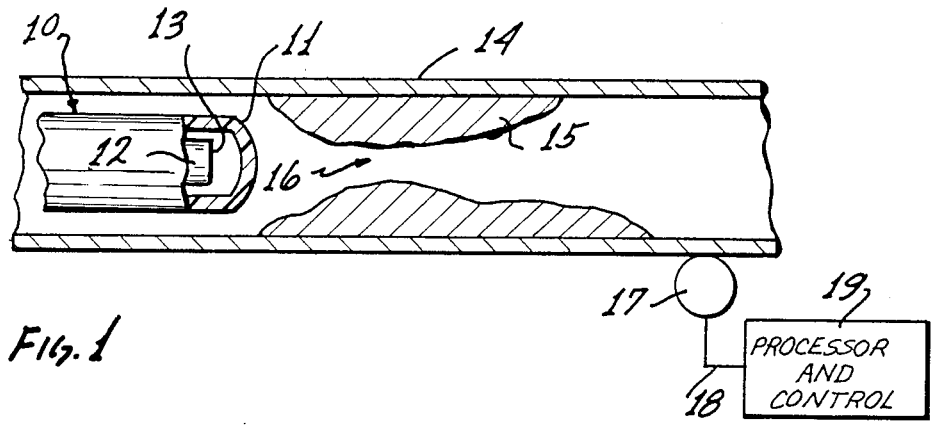
FIG. 1 is a cross sectional view of an artery showing placement of the sensor according to the intraoperative approach.

Referring now to FIG. 1, there is shown a probe or catheter 10 having a protective dome 11 over a fiber bundle 12. The bundle 12 extends within the catheter 10 according to known techniques to a distal end 13 of the bundle 12. The bundle 12 includes a plurality of individual laser delivery fibers (not individually shown in FIG. 1) that are adapted to be used in groups of one or more in delivering laser energy through the catheter 10 and dome 11 for purposes of subjecting targeted tissue to laser energy.

Use of a single fiber to ablate a therapeutically significant channel in an occluded vessel necessitates a large diameter light spot, and hence high laser power to provide enough intensity (power per unit area) for efficient ablation. Such high power can damage the surrounding tissue, which must dissipate all the energy delivered to the target site. Use of an array or bundle of fibers allows a set of small adjacent single-fiber craters, each produced by a small light spot at low laser power, to produce a large composite hole. Thus, a multifiber laser catheter is preferably used in the method of this invention, although a single fiber catheter may be employed without departing from certain aspects of the inventive method disclosed.

The catheter 10 is shown advanced within a vessel, such as an artery 14, according to known techniques to a position such that the distal end 13 of the bundle 12 is in proximity with a targeted lesion 15 within the artery 14. In this position, laser energy from a separate source (not shown in FIG. 1) is propagated through the bundle 12, and thus through the catheter 10, so that it passes through the dome 11 to the lesion 15. In this manner, the lesion 15 is subjected to laser energy for purposes of vaporizing a portion of the lesion 15.

The illustrated lesion 15 defines a channel 16, and vaporizing a portion of the lesion 15 constitutes an ablation process designed to enlarge the channel 16. However, laser energy missing the lesion 15 that passes through the channel 16 can damage the artery wall or artery 14 beyond the lesion 15. In addition, laser energy that vaporizes a sufficient portion of lesion 15, so that the laser energy breaks through the lesion 15, also threatens the artery 14.

The method of the invention includes placing a laser energy sensor in a monitoring position adapted to sense laser energy from the catheter 10 that passes beyond the lesion 15. This is accomplished with the illustrated catheter 10 by intraoperatively placing sensor 17 external to the artery 14 in a position beyond a portion of the lesion 15 to be subjected to laser energy. This is the monitoring position, i.e., a position beyond a portion of the lesion 15 to be subjected to laser energy, and the sensor 17 may be any of various known detector devices adapted to produce an electrical signal in response to laser energy passing through the artery 14 beyond the lesion 15.

The output of the laser energy sensor, sensor 17, is coupled over a line 18 to a suitable signal processing and control module 19, where it is processed and analyzed utilizing known circuitry and techniques. When the output of the sensor 17 is of a level indicating that the laser energy passing beyond the lesion 15 is more that a predetermined level (a level threatening to the artery 14), the module 19 produces a control signal to be used in controlling the laser energy. Control may include switching the laser energy on and off as well as varying power level and duration, and the control signal may be either an electrical signal for directly controlling the laser, or a human sensible signal designed to alert the physician. In either case, the control signal enables laser deactivation when a miss or breakthrough occurs that results in too much laser energy passing beyond the lesion 15.

Figure 2:
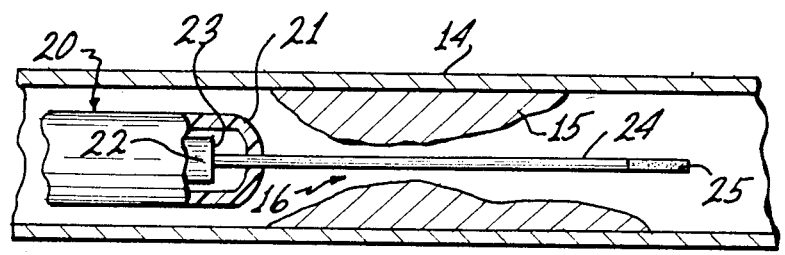
FIG. 2 is a cross sectional view similar to FIG. 2 showing sensor placement according to the percutaneous approach.

A percutaneous approach for doing this is illustrated in FIG. 2. A single fiber or a multifiber laser catheter 20 is used. The catheter 20 has a dome 21 and a bundle 22 extending to a distal end 23, which features are similar to the catheter 10. It includes a sensor fiber 24 having a distal end portion 25 that serves as the laser energy sensor.

The sensor fiber 24 is either fixed in or adapted to be selectively extended beyond the distal end 23 and the dome 21 to a position extending sufficiently beyond the distal end and dome to enable placement of the fiber 24 through the channel 16 to the monitoring position beyond the lesion 15. The sensor fiber 24 may be a clad fiber extending within the catheter 20 alongside the bundle 22, the distal end portion 25 of the sensor fiber 24 being unclad, roughened, or otherwise processed to enhance off axis collection of transmitted laser light. Laser energy passing beyond the lesion 15 passes through the sensor fiber 24 to suitable detection and processing circuitry that produces a control signal for use in controlling the laser energy.

Figure 3:
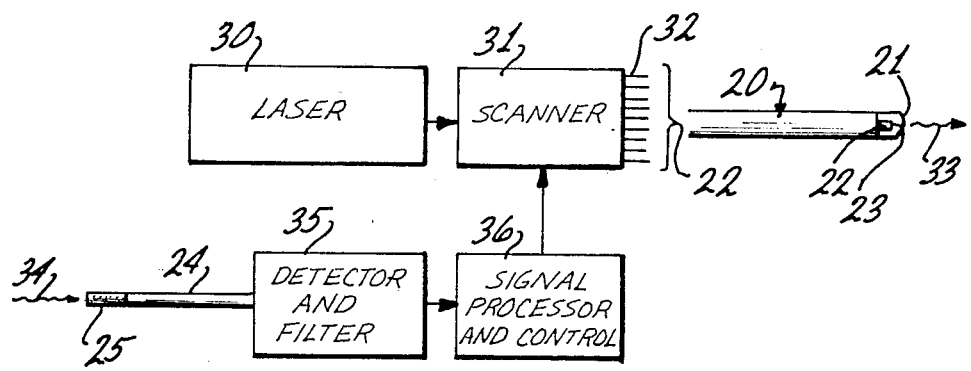
FIG. 3 of the drawings is a block diagram of a laser delivery system for removal arterial obstructions utilizing the percutaneous approach.

As shown in the block diagram of FIG. 3, laser energy from a laser 30 is controlled by a scanner 31 that couples the laser energy to a selected group of one or more fibers 22 of the bundle 22, preferably one fiber at a time. Laser energy depicted by an arrow 33 is propagated toward the lesion 15 in this manner, and a portion of the laser energy passing beyond the lesion 15, depicted by an arrow 34, is coupled by the sensor fiber 24 to a detector and filter circuit 35 that produces an electrical signal indicative of the level of the laser energy passing beyond the lesion 15.

This electrical signal is coupled to a signal processing and control circuit 36 that produces an electrical control signal that is used by the scanner 31 to control coupling of the laser energy from laser 30 to individual ones of the fibers 32 in the bundle 22, or alternatively, directly control the laser or a shutter placed in the path of the laser beam. Thus, a closed loop control system is provided that enables immediate laser deactivation and aiming by coupling the laser energy to selected ones of the fibers 32. If a threatening level of laser energy is detected beyond the lesion 15, the laser energy can be immediately deactivated, and laser energy coupled to only those fibers in a position to hit the lesion 15.

Thus, the invention overcomes various concerns of the prior art with a new and improved method of removing arterial obstructions. It monitors laser energy distally of the targeted lesion, and when a miss or breakthrough occurs, firing is terminated immediately, before damage occurs to the vessel wall. This, in combination with the multifiber laser catheter enables precise aiming and superior overall laser delivery.

Although an exemplary embodiment of the invention has been shown and described, many changes, modifications, and substitutions may be made by one having ordinary skill in the art without necessarily departing from the spirit and scope of this invention.

What is claimed is:

1. A laser delivery system, comprising:
   a catheter adapted to be advanced within a vessel to a position in which a distal end of the catheter is in proximity with a targeted lesion;
   at least one laser delivery fiber extending within the catheter to the distal end through which to propagate laser energy toward the lesion; and
   a laser energy sensor adapted to be placed in a monitoring position beyond the lesion and sense laser energy propagated through the laser delivery fibers that passes beyond the lesion;
   whereby the output of the sensor can be used to control the propagation of laser energy through the fiber in order to subject the lesion to laser energy without damaging the vessel wall beyond the lesion; and
   wherein the laser energy sensor includes a sensor fiber extending within the catheter and beyond the distal end to a position sufficiently beyond the distal end to extend through an opening in the lesion to the monitoring position.

2. A method of removing an obstruction from a vessel of the cardiovascular system with laser energy, comprising:
   advancing a laser delivery catheter within the vessel to a position in proximity with a targeted lesion in the vessel;
   placing a laser energy sensor in a monitoring position adapted to sense laser energy from the catheter that passes beyond the lesion;
   propagating laser energy through the catheter toward the lesion to subject the lesion to the laser energy; and
   controlling the laser energy according to the output of the sensor.

3. A method as recited in claim 2, wherein:

the sensor is placed external to the vessel.

4. A method as recited in claim 3, wherein:
the laser delivery catheter has a plurality of laser delivery fibers;
the step of advancing the laser delivery catheter includes advancing the catheter to a position in which the distal end of the laser delivery fibers are in proximity with the targeted lesion; and
the step of propagating laser energy includes propagating laser energy through selected ones of the laser delivery fibers according to the output of the sensor.

5. A method as recited in claim 4, wherein the step of propagating laser energy includes:
propagating laser energy through the laser delivery fibers in groups of one or more fibers, one group at a time.

6. A method as recited in claim 2, wherein:
the sensor is placed within the vessel.

7. A method as recited in claim 6, wherein:
the step of advancing a laser delivery catheter includes using a laser delivery catheter having a plurality of laser delivery fibers and a sensor fiber,
the step of advancing a laser delivery catheter further includes advancing the catheter to a position in which the distal end of the laser delivery fibers are in proximity with a targeted lesion and the sensor fiber extends beyond the lesion to a position adapted to sense laser energy passing beyond the lesion;
the step of propagating laser energy includes propagating laser energy through selected ones of the laser delivery fibers according to the output of the sensor.

8. A method as recited in claim 7, wherein the step of propagating laser energy includes:
propagating laser energy through the laser delivery fibers in groups of one or more fibers, one group at a time.

9. A method as recited in claim 2, wherein the step of controlling the laser energy includes:
producing a human sensible signal to alert an operator in the event more than a predetermined level of laser energy passes beyond the lesion.

10. A method as recited in claim 2, wherein the step of controlling the laser energy includes:
producing an electrical control signal to be used in controlling the laser in the event more than a predetermined level of laser energy passes beyond the lesion.

11. A method of removing an obstruction from a vessel of the cardiovascular system with a laser delivery catheter having a plurality of laser delivery fibers and a sensor fiber, comprising:
advancing the catheter to a position in which the distal end of the laser delivery fibers are in proximity with a targeted lesion and the sensor fiber extends beyond the lesion to a position adapted to sense laser energy passing beyond the lesion;
propagating laser energy through at least one of the laser delivery fibers toward the lesion;
processing the output of the sensor to produce an electrical signal to be used in controlling the laser energy according to the level of laser energy passing beyond the lesion as indicated by the output of the sensor; and
deactivating the laser energy with the electrical signal in the event more than a predetermined amount of laser energy passes beyond the lesion.

12. A method as recited in claim 11, wherein the step of processing the output of the sensor includes:
selecting a group of one or more fibers through which to propagate laser energy that is directed at a portion of the targeted lesion.

13. A method as recited in claim 11, wherein the step of processing the output of the sensor includes:
decoupling the laser energy from a fiber that is in a position to miss the lesion.

14. A laser delivery catheter, comprising:
a catheter body adapted to be advanced within a vessel to a position in which a distal end of the catheter body is in proximity with a targeted lesion;
at least one laser delivery fiber extending within the catheter body to the distal end through which to propagate laser energy toward the lesion; and
a sensor fiber extending within the catheter body and beyond the distal end to a position sufficiently beyond the distal end to extend through an opening in the lesion to a monitoring position beyond the lesion.

15. A laser delivery catheter, comprising:
a catheter body adapted to be advanced within a vessel to a position in which a distal end of the catheter body is in proximity with a targeted lesion;
at least one laser delivery fiber extending within the catheter body to the distal end through which to propagate laser energy toward the lesion; and
a sensor fiber extending within the catheter body, which sensor fiber is adapted to be selectively extended beyond the distal end to a position sufficiently beyond the distal end to extend through an opening in the lesion to a monitoring position beyond the lesion.

16. A laser delivery system, comprising:
a catheter adapted to be advanced within a vessel to a position in which a distal end of the catheter is in proximity with a targeted lesion;
at least one laser delivery fiber extending within the catheter to the distal end through which to propagate laser energy toward the lesion; and
a laser energy sensor adapted to be placed in a monitoring position beyond the lesion and sense laser energy propagated through the laser delivery fibers that passes beyond the lesion;
whereby the output of the sensor can be used to control the propagation of laser energy through the fiber in order to subject the lesion to laser energy without damaging the vessel wall beyond the lesion; and
wherein the laser energy sensor includes a sensor fiber extending within the catheter, which sensor fiber is adapted to be selectively extended beyond the distal end to a position sufficiently beyond the distal end to extend through an opening in the lesion to the monitoring position.

* * * * *